United States Patent [19]
Gerster

[11] 4,014,877
[45] * Mar. 29, 1977

[54] SUBSTITUTED BENZO[IJ]QUINOLIZINE-2-CARBOXYLIC ACIDS AND DERIVATIVES THEREOF

[75] Inventor: John F. Gerster, Woodbury, Minn.

[73] Assignee: Riker Laboratories, Inc., Northridge, Calif.

[ * ] Notice: The portion of the term of this patent subsequent to July 22, 1992, has been disclaimed.

[22] Filed: Jan. 22, 1975

[21] Appl. No.: 543,144

Related U.S. Application Data

[60] Division of Ser. No. 303,254, Nov. 2, 1972, Pat. No. 3,896,131, which is a continuation-in-part of Ser. No. 214,409, Dec. 30, 1971, abandoned.

[52] U.S. Cl. .............. 260/247.5 GP; 260/247.2 A; 260/287 P; 260/288 R; 260/289 R
[51] Int. Cl.² ...................................... C07D 413/06
[58] Field of Search ............ 260/247.2, 247.5, 287, 260/288, 289, 283, 247.2 A, 247.5 GP, 287 P, 288 R, 289 R

[56] References Cited
UNITED STATES PATENTS 3,524,858  8/1970  Kaminsky .......................... 260/287

*Primary Examiner*—G. Thomas Todd
*Attorney, Agent, or Firm*—Cruzan Alexander; Donald M. Sell

[57] ABSTRACT

Certain substituted 6,7-dihydro-1-oxo-1H,5H-benzo[ij]-quinolizine-2-carboxylic acids and hydrazides, esters, amides and salts thereof, intermediates therefor, and a process for their preparation are described; the compounds are active as anti-microbial agents.

5 Claims, No Drawings

SUBSTITUTED BENZO[IJ]QUINOLIZINE-2-CARBOXYLIC ACIDS AND DERIVATIVES THEREOF

RELATED APPLICATIONS

This is a division of application Ser. No. 303,254, filed Nov. 2, 1972, now U.S. Pat. No. 3,896,131, which is a continuation-in-part of application Ser. No. 214,409, filed Dec. 30, 1971, now abandoned.

BACKGROUND OF THE INVENTION

This invention relates to derivatives of the heterocyclic system known as benzo[ij]quinolizine. More specifically it relates to 6,7-dihydro-1-oxo-1H,5H-benzo[ij]quinolizine-2-carboxylic acids and salts, hydrazides, amides and esters thereof. These compounds are optionally substituted at the 5, 6 or 7 positions by lower alkyl groups and on the benzo ring portion by a variety of substituents. The use of these compounds as antimicrobial agents and pharmaceutical compositions containing these compounds are also included within the present invention.

Prior Art

The compound 2,3,6,7-tetrahydro-1-oxo-1H,5H-benzo[ij]-quinolizine has been reported (Mann and Smith, J. Chem. Soc. 1898 (1951)). So far as applicant is aware, the compound 6,7-dihydro-1-oxo-1H,5H-benzo[ij]quinolizine is not known to the art, nor are any derivatives thereof.

Detailed Description of the Invention

This invention relates to derivatives of 6,7-dihydro-1-oxo-1H,5H-benzo[ij]quinolizine. The structure and numbering system for this heterocyclic system are shown below:

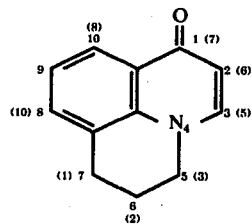

Referring to the structural formula above, this heterocyclic system may be named and numbered using the position number shown in italics in parenthesis, and that numbering system was used in the specification of application Ser. No. 214,409, which is the parent of the present application. However, the system represented by the plain numbers not in parenthesis is believed to be more in accordance with the rules of accepted Chemical Abstracts nomenclature, and this system will be used herein.

The compounds of the invention are carboxylic acids having the formula:

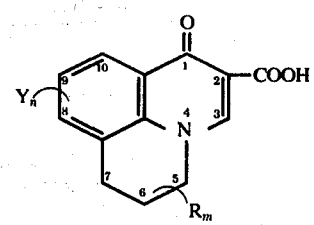

Formula I wherein Y is lower alkyl, lower alkoxy, halogen, hydroxy, nitro, cyano, trifluoromethyl, amino, lower alkanamido, trifluoroacetamido or N,N-lower dialkylamino, R is methyl, ethyl or trifluoromethyl, $n$ is an integer from zero to two, and when $n$ is two Y may be methylenedioxy ($-OCH_2O-$) or ethylenedioxy ($-OCH_2-CH_2O-$) bonded to adjacent ring positions, $m$ is an integer from zero to two, and when R is trifluoromethyl $m$ is one; and lower alkyl esters, acyl halides, acyl hydrazides, pharmaceutically acceptable salts or lower alkyl amides, morpholides or piperidides thereof.

"Lower alkyl" or "lower alkoxy" as used herein means alkyl or alkoxy, respectively, having from 1 to 4 carbon atoms in straight or branched chain configuration.

It is well known to the art that pharmaceutically acceptable salts such as alkali metal, alkaline earth, aluminum, iron and other metal and amine salts of pharmaceutically active acids are the equivalents of the acids, and in some cases may even offer advantages in absorption, formulation and the like.

Salts of the free acid compounds of the invention are readily prepared by reaction of the acid with a base and evaporation to dryness. The base may be organic, e.g. sodium methoxide or an amine, or inorganic.

The free acid compounds of the invention are presently preferred for some purposes owing to their having higher levels of anti-microbial activity than the corresponding esters. However, for agrichemical applications water-solubility is usually advantageous, and salts of the compounds of the invention are usually employed in formulations for this purpose. The esters and acyl halides are useful for preparation of the corresponding acids, and they, as well as the acyl hydrazides, salts and the amides, are also useful for modifying solubility and persistence of the compounds under conditions of use.

Compounds of the invention wherein $m$ is one and R is methyl are preferred.

When Y is halogen this can be fluorine, chlorine, bromine or iodine. Presently preferred are fluorine and chlorine.

It is presently preferred that Y be methyl, methylenedioxy, ethylenedioxy, methoxy, acetamido, fluorine or chlorine. When $n$ is greater than one, each Y may be the same or a differing substituent.

The anti-microbial activity of the compounds of the present invention can be demonstrated by the known, standard plate dilution method for bacterial susceptibility to antibiotics. The culture medium employed permits susceptibility testing of fastidious microorganisms towards antibiotics, sulfonamides and other chemotherapeutic agents. Tryptone soy agar (oxoid) of the following composition is the culture medium.

| | |
|---|---|
| Oxoid tryptone | 15 g. |
| Oxoid soy peptone | 5 g. |

-continued

| | |
|---|---|
| Sodium chloride | 5 g. |
| Oxoid agar-agar No. 3 | 15 g. |
| Water | 1 liter |

Using this test, the compounds of the invention have been found to have a broad spectrum of activity against gram-positive and gram-negative microorganisms.

The compounds of the invention are active against microorganisms either in the absence or presence of ten percent horse serum.

The test procedure used to determine activity as employed in connection with the present invention provides information on the amount of a compound required to give complete inhibition, partial inhibition or no inhibition of microbial growth on the agar plates. In the tests, the selected compound is added to the agar medium to give concentrations of zero, one, ten and one hundred milligrams per liter. A series of plates with these concentrations is prepared. Ten percent horse serum is added to one series of such plates. Aliquots of broth culture of each of eleven species of microorganisms are innoculated into the agar plates containing the various compound concentrations. The plates are incubated at 37° C. in a ten percent carbon dioxide atmosphere for 18 to 24 hours. The microbial growth on each plate is read visually, and minimal inhibitory concentrations are recorded.

The microorganisms used for this test were:
1. *Staphylococcus aureus*
2. *Bacillus subtilus*
3. *Pseudomonas aeruginosa*
4. *Escherichia coli*
5. *Streptococcus sp.*
6. *Aspergillus niger*
7. *Candida albicans*
8. *Mima polymorpha*
9. *Herellea vaginicola*
10. *Klebsiella pneumoniae*
11. *Streptococcus fecaelis*

*Strains isolated from dental caries in rats or hamsters at the National Institute of Dental Health and grown in PFY or APT agar.

All of the compounds of the invention possess antimicrobial activity towards one or more of the above microorganisms.

Many of the compounds of the invention have also shown activity towards anaerobic bacteria, for example *Bacteroides sp.* and *Clostridium welchii*. Some compounds of the invention have shown useful activity towards *Erwinia amylovora*, a gram-negative microorganism responsible for the plant disease known as fire blight.

It will be understood by those skilled in the art that the species used are representative indicator species, as it would be impractical to screen against all bacteria. It is well known in the art that broad spectrum activity can be predicted on the activity shown against selected representative bacterial species.

Many of the compounds of the invention are active when administered orally to animals. They are excreted in the urine, and are effective urinary tract antibacterials in mammals.

All of the compounds of the invention are active against microorganisms in vitro or topically. In vitro activity is useful in itself, since anti-microbial agents may be used for disinfecting and sterilizing, for example medical and dental equipment, as components of disinfecting solutions. The preferred compounds of the invention are also active in vivo in animals.

The acute oral toxicity of the compounds of the invention generally is moderate to low compared with the effective oral dose, and they have a fair to excellent therapeutic ratio.

Presently preferred compounds of the invention have a broad spectrum of anti-microbial activity and a good therapeutic ratio ($LD_{50}/ED_{50}$). These compounds are:
6,7-dihydro-5,10-dimethyl-1-oxo-1H,5H-benzo[ij]-quinolizine-2-carboxylic acid,
9-chloro-6,7-dihydro-5-methyl-1-oxo-1H,5H-benzo[ij]quinolizine-2-carboxylic acid,
sodium 6,7-dihydro-9-fluoro-5-methyl-1-oxo-1H,5H-benzo[ij]quinolizine-2-carboxylate hydrate,
methyl 6,7-dihydro-9-fluoro-5-methyl-1-oxo-1H,5H-benzo[ij]quinolizine-2-carboxylate,
6,7-dihydro-9-fluoro-5-methyl-1-oxo-1H,5H-benzo[ij]quinolizine-2-carboxamide,
10-acetamido-6,7-dihydro-5-methyl-1-oxo-1H,5H-benzo[ij]quinolizine-2-carboxylic acid,
6,7-dihydro-5,8,10-trimethyl-1-oxo-1H,5H-benzo[ij]quinolizine-2-carboxylic acid,
8-chloro-6,7-dihydro-5-methyl-1-oxo-1H,5H-benzo[ij]quinolizine-2-carboxylic acid,
6,7-dihydro-8-methoxy-5-methyl-1-oxo-1H,5H-benzo[ij]quinolizine-2-carboxylic acid,
6,7-dihydro-5,7-dimethyl-9-fluoro-1-oxo-1H,5H-benzo[ij]quinolizine-2-carboxylic acid,
6,7-dihydro-5,8-dimethyl-1-oxo-1H,5H-benzo[ij]-quinolizine-2-carboxylic acid,
2,3-dihydro-3-methyl-7-oxo-1H,7H-1,3-dioxo[9,10-]benzo[ij]quinolizine-6-carboxylic acid,
3-methyl-7-oxo-2,3,10,11-tetrahydro-1H,7H-1,4-dioxino[9,10]benzo[ij]quinolizine-6-carboxylic acid,
6,7-dihydro-9-fluoro-5-methyl-1-oxo-1H,5H-benzo[ij]quinolizine-2-carboxylic acid and
6,7-dihydro-9-fluoro-1-oxo-5-trifluoromethyl-1H,5H-benzo[ij]quinolizine-2-carboxylic acid.

The acidic compounds of the invention are ordinarily white or yellowish to brown crystalline or amorphous materials when purified. They are substantially insoluble in water, lower alcohols or hydrocarbons and are more soluble in halogenated solvents, dimethylformamide and the like. The esters and amides are generally somewhat more soluble in organic solvents. The alkali metal salts have appreciable solubility in water and lower alcohols.

The compounds of the invention may be formulated by incorporating them into conventional pharmaceutical carrier materials, either organic or inorganic, which are suitable for oral or intraperitoneal application. For in vitro or topical use, simple aqueous solutions or suspensions are most conveniently employed. For this purpose, concentrations of the order of 100 parts per million up to about 5 parts per thousand are suitable, and the formulation is used by immersing objects to be treated therein, or by local application to an infected area.

The amount of compound to be used for e.g. oral treatment of a microbial urinary infection will be an effective amount less than a toxic amount. The amount to be administered to control an infection will depend on the species, sex, weight, physical condition and many other factors, but this judgment is well within the skill of the medical art. Usually the amount will be less than 100 mg/kg. per dose. Conveniently this is administered in the form of the usual pharmaceutical preparation such as capsules, tablets, emulsions, solutions and the like. Excipients, fillers, coatings, etc. are employed with tablets or capsules, as well known in the art.

It is known to the art that anti-microbial agents are used as growth promoters in various animal and bird species. Although not yet verified, it is inferred from the outstanding anti-microbial activity that the compounds of the invention can be used for this purpose also. The compounds of the invention may also be used for the control of microbial (e.g. *Erwinia amylovora*) infections of plants, e.g. by spraying or dusting formulations of these compounds on the affected area.

The compounds of the invention are prepared starting with a tetrahydroquinoline as illustrated by the following reaction sequence, in which Y and R have the same significance as hereinabove, and "alk" means lower alkyl, preferably ethyl.

of Formula I. Other esters and salts with metals or amines can be prepared from the acids by known methods, e.g. simple neutralization with an equivalent of base in an organic solvent, followed by evaporation.

Amides of the acidic compounds of the invention are prepared by conventional techniques, e.g. by reacting the corresponding acid of Formula I with, e.g. thionyl chloride, then reacting the acid chloride with ammonia or an amine to provide the amide. Hydrazides of the invention are prepared by conventional methods, e.g. by reacting the corresponding ester with hydrazine in a suitable solvent such as an alcohol.

Many tetrahydroquinolines of Formula II are known. Others may be prepared by known procedures from intermediates. For example, compounds of Formula II may be conveniently prepared by one of the following methods:

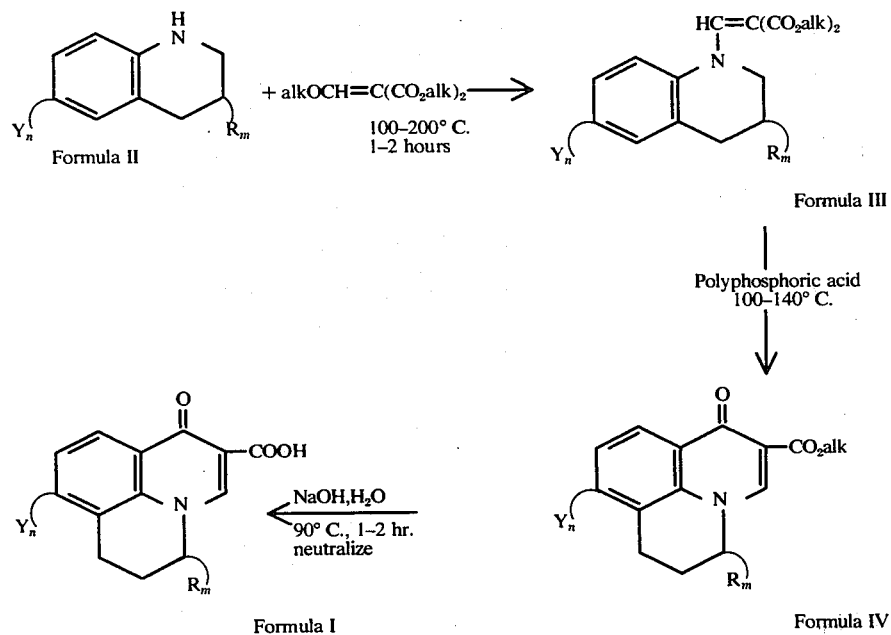

In the above reaction sequence a dialkyl alkoxymethylenemalonate is condensed with a tetrahydroquinoline of Formula II by heating without solvent at 100° to 200° C. for one to five hours. The novel intermediates, Formula III, are generally oils which need not be isolated or purified. Instead, polyphosphoric acid is added, and the solution is heated at 100° to 140° C. to effect a condensation to the esters of Formula IV. The esters of Formula III are likewise included within the scope of the invention. The final step, if desired, is saponification of the esters of Formula IV to the acids Procedure A

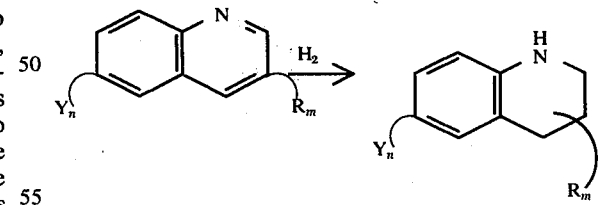

wherein Y, *n*, R and *m* are as hereinabove defined.

Procedure B

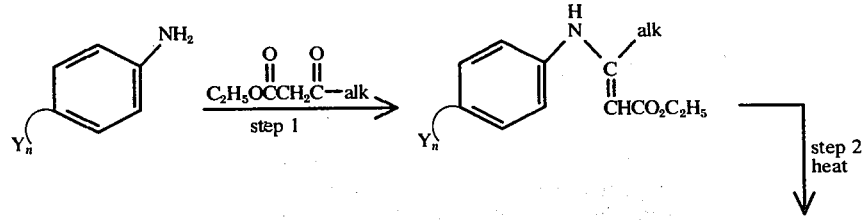

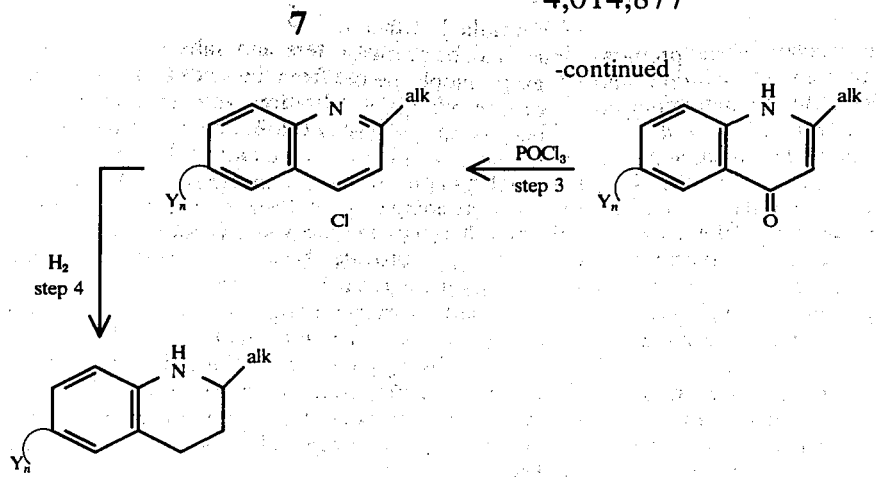

wherein Y, n and alk are as hereinabove defined.

In procedure A catalytic reduction methods, using e.g. rhodium on carbon or platinum on carbon in a suitable solvent such as ethanol are conveniently used.

In procedure B, comprising known reactions, step 1 can be carried out by direct reaction without solvent, by reaction of an acylacetic ester with an aniline in the presence of acid catalyst, or steps 1 and 2 may be combined and run without isolation of the intermediate of step 1, in polyphosphoric acid. Step 2 is run by heating in a high boiling solvent such as Dowtherm A (a mixture of biphenyl and phenoxybenzene). Step 3 is a well-known aromatizing and halogenating reaction. Step 4 employs catalytic reduction, preferably using rhodium on carbon or platinum on carbon in ethanol.

In a variation of procedure B, the starting aniline has an ortho chloro substituent which is removed after step 2 by reduction in aqueous alkaline (sodium or potassium hydroxide) ethanol with Raney nickel catalyst. Steps 3 and 4 then proceed as illustrated.

Compounds of the invention wherein Y is lower alkanamido are prepared by the reaction of the corresponding aromatic amines with lower acyl halides or anhydrides.

Compounds of the invention wherein Y is hydroxy may be prepared by simple cleavage of the corresponding alkoxy compounds using well-known methods, for example heating with hydrobromic acid.

Compounds of the invention wherein Y is nitro are optionally prepared by direct nitration of other compounds of the invention, and the corresponding amino derivatives can be formed by reduction of the nitro group with basic Raney nickel.

Compounds of the invention wherein Y is amino can also be converted by known methods through the diazonium salts to compounds wherein Y is cyano or halogen.

The following non-limiting examples are provided to illustrate the synthetic methods useful to obtain compounds of the invention, and the compounds thus obtained.

EXAMPLE 1

2,6-Dimethyltetrahydroquinoline (32.2 g., 0.2 mole) is mixed with diethyl ethoxymethylenemalonate, and the mixture is heated at 125° to 130° C. for three hours. Polyphosphoric acid (200 g.) is added, and the solution is gradually heated to 115° to 120° C. in an oil bath with occasional stirring. The temperature is maintained for one hour, then the mixture is poured into 600 ml. of water and neutralized with 40 percent sodium hydroxide solution. The product ester of Formula III which precipitates is separated by filtration, washed with water and suspended in two liters of 10 percent sodium hydroxide solution. The mixture is heated on the steam bath for one hour, treated with decolorizing charcoal, filtered, then neutralized with concentrated hydrochloric acid. The solid product is isolated by filtration of the hot solution, washed with water and recrystallized from dimethylformamide. The white, crystalline product is 6,7-dihydro-5,9-dimethyl-1-oxo-1H,5H-benzo[ij]-quinolizine-2-carboxylic acid, m.p. 255°–257° C.

Analysis: Calculated for $C_{15}H_{15}NO_3$: C, 70.0; H, 5.9; N, 5.45. Found: C, 70.0; H, 5.7; N, 5.4.

EXAMPLE 2

Following the procedure set forth in Example 1, 2-ethyltetrahydroquinoline is mixed with diethyl ethoxymethylenemalonate and heated to 125° to 130° C. for two hours. Polyphosphoric acid is added, and the mixture is heated at 115° C. for one hour. The mixture is poured into water, neutralized with 40 percent sodium hydroxide, and the product is isolated and saponified in 10 percent sodium hydroxide solution. The solution is neutralized, and the solid product, 6,7-dihydro-5-ethyl-1-oxo-1H,5H-benzo[ij]quinolizine-2-carboxylic acid, is isolated by filtration.

Using the procedure of Example 1 and starting with the appropriately substituted tetrahydroquinolines, the compounds of Table I are prepared.

TABLE I

| Ex. No. | Compound | Melting Point (in ° C.) |
|---|---|---|
| 3 | 6,7-dihydro-9-fluoro-5-methyl-1-oxo-1H,5H-benzo[ij]quinolizine-2-carboxylic acid | 253–255 |
| 4 | 9-chloro-6,7-dihydro-5-methyl-1-oxo-1H,5H-benzo[ij]quinolizine-2-carboxylic acid | 251–253 |
| 5 | 6,7-dihydro-9-(N,N-dimethylamino)-5-methyl-1-oxo-1H,5H-benzo[ij]-quinolizine-2-carboxylic acid | 241–243 |
| 6 | 6,7-dihydro-5,10-dimethyl-1-oxo-1H,5H-benzo[ij]quinolizine-2-carboxylic acid | 179–180 |
| 7 | 8-chloro-6,7-dihydro-5,9-dimethyl-1-oxo-1H,5H-benzo[ij]quinolizine-2-carboxylic acid | 288–290 |
| 8 | 6,7-dihydro-9,10-dimethoxy-5-methyl-1-oxo-1H,5H-benzo[ij]quinolizine-2-carboxylic acid | 220–223 |
| 9 | 6,7-dihydro-1-oxo-5,8,10-trimethyl-1H,5H-benzo[ij]quinolizine-2-carboxylic acid | 188–190 |
| 10 | 6,7-dihydro-9-methoxy-5-methyl-1-oxo- | |

TABLE I-continued

| Ex. No. | Compound | Melting Point (in °C.) |
|---|---|---|
|  | 1H,5H-benzo[ij]quinolizine-2-carboxylic acid | 208–210 |
| 11 | 6,7-dihydro-10-methoxy-5-methyl-1-oxo-1H,5H-benzo[ij]quinolizine-2-carboxylic acid | 244–246 |
| 12 | 6,7-dihydro-5-methyl-1-oxo-1H,5H-benzo[ij]quinolizine-2-carboxylic acid | 231–232 |
| 13 | 9-bromo-6,7-dihydro-5-methyl-1-oxo-1H,5H-benzo[ij]quinolizine-2-carboxylic acid | 249–251 |
| 14 | 6,7-dihydro-8-methoxy-5-methyl-1-oxo-1H,5H-benzo[ij]quinolizine-2-carboxylic acid | 233–235.5 |
| 15 | 6,7-dihydro-5,8-dimethyl-1-oxo-1H,5H-benzo[ij]quinolizine-2-carboxylic acid | 264–265 |
| 16 | 6,7-dihydro-8,9-dimethoxy-5-methyl-1-oxo-1H,5H-benzo[ij]quinolizine-2-carboxylic acid | 235–237 |
| 17 | 2,3-dihydro-3-methyl-7-oxo-1H,7H-1,3-dioxolo[9,10]benzo[ij]quinolizine-6-carboxylic acid | >300 |
| 18 | 3-methyl-7-oxo-2,3,10,11-tetrahydro-1H,7H-1,4-dioxino[9,10]benzo[ij]quinolizine-6-carboxylic acid | >300 |
| 19 | 6,7-dihydro-5-methyl-1-oxo-1H,5H-1,3-dioxolo[9,10]benzo[ij]quinolizine-2-carboxylic acid | >305 |
| 20 | 8-chloro-6,7-dihydro-9-methoxy-5-methyl-1-oxo-1H,5H-benzo[ij]quinolizine-2-carboxylic acid | 246–248 |
| 21 | 6,7-dihydro-5,7-dimethyl-9-fluoro-1-oxo-1H,5H-benzo[ij]quinolizine-2-carboxylic acid | 208–209 |
| 22 | 6,7-dihydro-7-ethyl-5-methyl-1-oxo-1H,5H-benzo[ij]quinolizine-2-carboxylic acid | 205–207 |
| 23 | 6,7-dihydro-9-fluoro-1-oxo-1H,5H-benzo[ij]quinolizine-2-carboxylic acid |  |
| 24 | 6,7-dihydro-5-methyl-1-oxo-8-trifluoromethyl-1H,5H-benzo[ij]quinolizine-2-carboxylic acid |  |

EXAMPLE 25

6-(N,N-Dimethylamino)-2-methyltetrahydroquinoline (25 g., 0.132 mole) is mixed with diethyl ethoxymethylenemalonate (28.4 g., 0.132 mole), and the mixture is heated at 120° C. for three hours. Polyphosphoric acid (200 g.) is added, and the solution is heated gradually to 120° C. with occasional stirring. The solution is maintained at 120° to 130° C. for one hour then poured into 500 ml. of water, with stirring. The solution is neutralized with 40 percent sodium hydroxide solution. The yellow product is separated by filtration and recrystallized from ethanol giving ethyl 6,7-dihydro-9-(N,N-dimethylamino)-5-methyl-1-oxo-1H,5H-benzo[ij]quinolizine-2-carboxylate, m.p. 219°–222° C.

Analysis: Calculated for $C_{20}H_{26}N_2O_3$: C, 68.9; H, 7.1; N, 8.9. Found: C, 68.6; H, 7.0; N, 8.9.

EXAMPLE 26

Using the procedure of Example 25, 2,7-dimethyltetrahydroquinoline and diethyl ethoxymethylenemalonate are reacted to give solid ethyl 6,7-dihydro-5,10-dimethyl-1-oxo-1H,5H-benzo[ij]quinolizine-2-carboxylate, m.p. 106°–108° C.

Analysis: Calculated for $C_{17}H_{19}NO_3$: C, 71.6; H, 6.7; N, 4.9. Found: C, 71.5; H, 6.9; N, 4.9.

Using the procedure of Example 25, the compounds of Table II are prepared.

TABLE II

| Ex. No. | Compound | Melting Point (°C.) |
|---|---|---|
| 27 | ethyl 6,7-dihydro-9-fluoro-5-methyl-1-oxo-1H,5H-benzo[ij]quinolizine-2-carboxylate | 176–178 |
| 28 | ethyl 9-chloro-6,7-dihydro-5-methyl-1-oxo-1H,5H-benzo[ij]quinolizine-2-carboxylate |  |
| 29 | ethyl 8-chloro-6,7-dihydro-5,9-dimethyl-1-oxo-1H,5H-benzo[ij]quinolizine-2-carboxylate | 190–192 |
| 30 | ethyl 6,7-dihydro-9-methoxy-5-methyl-1-oxo-1H,5H-benzo[ij]quinolizine-2-carboxylate |  |
| 31 | ethyl 6,7-dihydro-5-methyl-1-oxo-1H,5H-benzo[ij]quinolizine-2-carboxylate |  |
| 32 | ethyl 6,7-dihydro-5,9-dimethyl-1-oxo-1H,5H-benzo[ij]quinolizine-2-carboxylate |  |
| 33 | ethyl 9-bromo-6,7-dihydro-5-methyl-1-oxo-1H,5H-benzo[ij]quinolizine-2-carboxylate | 243–245 |
| 34 | ethyl 6,7-dihydro-9-fluoro-1-oxo-5-trifluoromethyl-1H,5H-benzo[ij]quinolizine-2-carboxylate | 200–202 |
| 35* | methyl 6,7-dihydro-9-fluoro-5-methyl-1-oxo-1H,5H-benzo[ij]quinolizine-2-carboxylate | 232–234 |

*The starting material is dimethyl ethoxymethylenemalonate.

EXAMPLE 36

Diethyl ethoxymethylenemalonate (43.2 g., 0.20 mole) and 6-methoxytetrahydroquinoline (32.6 g., 0.20 mole) are mixed and heated at 125°–130° C. for three hours. Polyphosphoric acid (200 g.) is added, and the mixture is heated gradually to 220° C. then maintained at 220° C. for one hour. The mixture containing the product ester of Formula III is poured into about 600 ml. of water, then made basic with 40 percent sodium hydroxide solution and heated on a steam bath for two hours. The solution is treated with decolorizing charcoal, filtered and acidified. The solid product is isolated by filtration, washed with water and ethanol, then recrystallized from N,N-dimethylformamide to give 6,7-dihydro-9-methoxy-1-oxo-1H,5H-benzo[ij]quinolizine-2-carboxylic acid, m.p. 253°–257° C.

Analysis: Calculated for $C_{14}H_{13}NO_4$: C, 64.9; H, 5.1; N, 5.4. Found: C, 64.8; H, 5.0; N, 5.4.

Other compounds prepared according to Example 36 are described in Table III.

TABLE III

| Ex. No. | Compound | Melting Point (°C.) |
|---|---|---|
| 37 | 9-chloro-6,7-dihydro-1-oxo-1H,5H-benzo[ij]quinolizine-2-carboxylic acid | 281–283 |
| 38 | 6,7-dihydro-1-oxo-1H,5H-benzo[ij]quinolizine-2-carboxylic acid | 278.5–282 |

Compounds of the invention of Formula III prepared according to Example 25 are described in Table IV.

TABLE IV

| Ex. No. | Compound |
|---|---|
| 39 | ethyl 6,7-dihydro-1-oxo-1H,5H-benzo[ij]quinolizine-2-carboxylate |
| 40 | ethyl 6,7-dihydro-9-methoxy-1-oxo-1H,5H-benzo[ij]-quinolizine-2-carboxylate |
| 41 | ethyl 9-chloro-6,7-dihydro-1-oxo- |

TABLE IV-continued

| Ex. No. | Compound |
|---|---|
|  | 1H,5H-benzo[ij]-quinolizine-2-carboxylate |

EXAMPLE 42

A solution of 6,7-dihydro-1-oxo-1H,5H-benzo[ij]-quinolizine-2-carboxylic acid (4.6 g., 0.02 mole) in concentrated sulfuric acid (30 ml.) is treated with a mixture of 30 ml. of concentrated sulfuric acid and 2 ml. of concentrated nitric acid, keeping the temperature below 30° C. The resulting solution is stirred at 25° C. for 24 hours, poured over ice and treated with ammonium hydroxide to pH 1 to 2. The mixture is filtered, slurried in methanol, and the solid product is separated by filtration. The product, 6,7-dihydro-10-nitro-1-oxo-1H,5H-benzo[ij]quinolizine-2-carboxylic acid, is recrystallized from N,N-dimethyl formamide to give yellow needles, m.p. 295° C. (dec.).

It had earlier been assumed, based on the known nitration of quinoline derivatives, that nitration of the 6,7-dihydro-1-oxo-1H,5H-benzo[ij]quinolizine-2-carboxylic acids would occur in the 9 position. Earlier structural assignments of nitro compounds of the invention prepared by nitration as described in Example 42, and amino and acetamido derivatives prepared therefrom, were in error. It has been established by high resolution nuclear magnetic resonance spectroscopic analysis that nitration occurs in the 10 position when the benzo ring is otherwise unsubstituted.

Analysis: Calculated for $C_{13}H_{10}N_2O_5$: C, 56.9; H, 3.7; N, 10.2. Found: C, 57.0; H, 3.5; N, 10.4.

Using the procedure of Example 42 the following compounds are prepared.

EXAMPLE 43

6,7-Dihydro-5,10-dimethyl-9-nitro-1-oxo-1H,5H-benzo[ij]quinolizine-2-carboxylic acid, m.p. 273°–275° C.

EXAMPLE 44

6,7-Dihydro-5-methyl-10-nitro-1-oxo-1H,5H-benzo[ij]quinolizine-2-carboxylic acid, m.p. >300° C.

EXAMPLE 45

Solid 6,7-dihydro-5-methyl-9-methoxy-1-oxo-1H,5H-benzo[ij]quinolizine-2-carboxylic acid (9.9 g., 0.035 mole) is added to 48 percent aqueous hydrobromic acid (100 ml.), and the mixture is refluxed six hours. The mixture is diluted with water, and the resulting solid precipitate is separated by filtration. The solid is dissolved in hot 10 percent sodium hydroxide solution and reprecipitated by the addition of concentrated hydrochloric acid. The product is collected by filtration, washed with water and ethanol and dried. The off-white solid is 6,7-dihydro-9-hydroxy-1-oxo-1H,5H-benzo[ij]quinolizine-2-carboxylic acid, m.p. >290° C. (dec.). Analysis: Calculated for $C_{14}H_{13}NO_4$: C, 64.8; H, 5.06; N, 5.4. Found: C, 65.1; H, 4.90; N, 5.4.

EXAMPLE 46

6,7-Dihydro-5-methyl-10-nitro-1-oxo-1H,5H-benzo[ij]quinolizine-2-carboxylic acid (10 g., 0.0345 mole) is dissolved in 300 ml. of aqueous potassium hydroxide (1.9 g., 0.0345 mole) and hydrogenated on a Parr apparatus using Raney nickel catalyst, initial hydrogen pressure 50 p.s.i. The mixture is filtered, and the filtrate is brought to pH 6 with concentrated hydrochloric acid. The yellow precipitate is separated by filtration, washed with water, dried, then recrystallized from N,N-dimethyl formamide to give 10-amino-6,7-dihydro-5-methyl-1-oxo-1H,5H-benzo[ij]quinolizine-2-carboxylic acid, m.p. 247°–249° C.

EXAMPLE 47

Using the procedure of Example 45, 6,7-dihydro-8-methoxy-5-methyl-1-oxo-1H,5H-benzo[ij]quinolizine-2-carboxylic acid is reacted with hydrobromic acid to provide 6,7-dihydro-8-hydroxy-5-methyl-1-oxo-1H,5H-benzo[ij]quinolizine-2-carboxylic acid, m.p. >300° C.

EXAMPLE 48

Using the method of Example 46, 6,7-dihydro-10-nitro-1H,5H-benzo[ij]quinolizine-2-carboxylic acid is reduced to provide 10-amino-6,7-dihydro-1-oxo-1H,5H-benzo[ij]quinolizine-2-carboxylic acid, m.p. >300° C.

Analysis: Calculated for $C_{13}H_{12}N_2O_3$: C, 63.9; H, 5.0; N, 11.5. Found: C, 63.6; H, 4.8; N, 11.5.

EXAMPLE 49

10-Amino-6,7-dihydro-5-methyl-1-oxo-1H,5H-benzo[ij]quinolizine-2-carboxylic acid (5.0 g., 0.018 mole) and acetic anhydride (50 ml.) are stirred and heated on a steam bath for three hours. After cooling, the solid precipitate is separated by filtration, washed with water, dried, then recrystallized from N,N-dimethyl formamide to provide 10-acetamido-6,7-dihydro-5-methyl-1-oxo-1H,5H-benzo[ij]quinolizine-2-carboxylic acid, m.p. 227°–279° C.

Analysis: Calculated for $C_{14}H_{14}N_2O_3$: C, 64.0; H, 5.4; N, 9.3 Found: C, 63.8; H, 5.3; N, 9.3.

EXAMPLE 50

Using the method of Example 49, the acid is reacted with trifluoroacetic anhydride to provide 6,7-dihydro-5-methyl-1-oxo-10-trifluoroacetamido-1H,5H-benzo[ij]quinolizine-2-carboxylic acid, m.p. 301°–303° C.

EXAMPLE 51

Using the method of Example 49, 8-amino-9-chloro-6,7-dihydro-5-methyl-1-oxo-1H,5H-benzo[ij]quinolizine-2-carboxylic acid is reacted with acetic anhydride to provide 8-acetamido-9-chloro-6,7-dihydro-5-methyl-1-oxo-1H,5H-benzo[ij]quinolizine-2-carboxylic acid, m.p. 234°–236° C.

EXAMPLE 52

Using the method of Example 49, 10-amino-6,7-dihydro-1-oxo-1H,5H-benzo[ij]quinolizine-2-carboxylic acid is reacted with acetic anhydride to provide 10-acetamido6,7-dihydro-1-oxo-1H,5H-benzo[ij]quinolizine-2-carboxylic acid, m.p. >300° C.

EXAMPLE 53

Using the method of Example 49, 10-amino-6,7-dihydro-5-methyl-1-oxo-1H,5H-benzo[ij]quinolizine-2-carboxylic acid is reacted with n-propionic anhydride to provide 6,7-dihydro-5-methyl-1-oxo-10-n-propionamido-1H,5H-benzo[ij]quinolizine-2-carboxylic acid, m.p. 253°–255° C.

EXAMPLE 54

Using the method of Example 49, 10-amino-6,7-dihydro-5-methyl-1-oxo-1H,5H-benzo[ij]quinolizine-2-carboxylic acid is reacted with n-butyric anhydride to provide 10-n-butyramido-6,7-dihydro-5-methyl-1-oxo-1H,5H-benzo[ij]quinolizine-2-carboxylic acid, m.p. 225°–227° C.

EXAMPLE 55

6,7-Dihydro-9-fluoro-5-methyl-1-oxo-1H,5H-benzo[ij]-quinolizine-2-carboxylic acid (31 g., 0.12 mole), sodium hydroxide (4.75 g., 0.12 mole) and ethanol (300 ml.) are mixed, and about 85 ml. of water are added with stirring. After one hour the mixture is filtered, then the filtrate is evaporated to dryness. The residue is azeotroped twice with an ethanol-benzene mixture. The solid is dissolved in methanol, the solution is filtered, and the product is precipitated by the addition of diethyl ether. The product is sodium 6,7-dihydro-9-fluoro-5-methyl-1-oxo-1H,5H-benzo[ij]quinolizine-2-carboxylate hydrate, m.p. >195° C.

Analysis: Calculated for $C_{14}H_{11}FNNaO_3 \cdot \frac{3}{4} H_2O$: C, 56.8; H, 4.3; N, 4.7. Found: C, 56.6; H, 4.4; N, 4.7.

EXAMPLE 56

A. Preparation of an acyl chloride derivative 6,7-Dihydro-9-fluoro-5-methyl-1-oxo-1H,5H-benzo[ij]quinolizine-2-carboxylic acid (5.0 g., 0.0192 mole) is stirred with thionyl chloride (75 ml.), and the mixture is heated to its reflux temperature and maintained at reflux for about 18 hours. The mixture is evaporated to dryness, then azeotroped thrice with 50 ml. portions of benzene to provide an off-white solid, 6,7-dihydro-9-fluoro-5-methyl-1-oxo-1H,5H-benzo[ij]quinolizine-2-carboxyl chloride, m.p. 183°–186° C.

B. Preparation of an amide derivative

The product of part A (5.4 g., 0.192 mole) is added to 100 ml. of ammonium hydroxide with stirring and stirred for four hours. The yellow precipitate is separated by filtration, washed with water, then recrystallized from ethanol to provide 6,7-dihydro-9-fluoro-5-methyl-1-oxo-1H,5H-benzo[ij]quinolizine-2-carboxamide hydrate, m.p. >300° C.

Analysis: Calculated for $C_{14}H_{13}FN_2O_2 \cdot H_2O$: C, 60.3; H, 5.4; N, 10.0. Found: C, 60.2; H, 5.4; N, 9.8.

Additional compounds prepared according to the method of Example 56 and using other amines as starting materials are given in Table V.

TABLE V

| Ex. No. | Compound | Melting Point (in ° C.) |
|---|---|---|
| 57 | N,N-dimethyl-6,7-dihydro-9-fluoro-5-methyl-1-oxo-1H,5H-benzo[ij]-quinolizine-2-carboxamide | 242–244 |
| 58 | 6,7-dihydro-9-fluoro-5-methyl-1-oxo-1H,5H-benzo[ij]quinolizine-2-carboxylic acid morpholine amide | 253–256 |

EXAMPLE 59

Ethyl 6,7-dihydro-9-fluoro-5-methyl-1-oxo-1H,5H-benzo-[ij]quinolizine-2-carboxylate (10 g., 0.0347 mole) is dissolved in methanol (200 ml.) containing 25 ml. of 97 percent hydrazine. The mixture is warmed to accelerate solution. The solution is stirred at room temperature, and solid begins to separate immediately. The solid is separated by filtration, washed with methanol and recrystallized from aqueous ethanol to provide 6,7-dihydro-9-fluoro-5-methyl-1-oxo-1H,5H-benzo[ij]quinolizine-2-carboxylic acid hydrazide, m.p. 236°–238° C.

Analysis: Calculated for $C_{14}H_{14}N_3O_2F$: C, 61.1; H, 5.1; N, 15.3. Found: C, 61.4; H, 5.1; N, 15.5.

EXAMPLE 60

6-Fluoro-2-trifluoromethyltetrahydroquinoline is condensed with an equimolar amount of diethylethoxymethylenemalonate according to the method of Example 1. The ester intermediate of Formula III is hydrolyzed according to Example 1, and the solid product is recrystallized from N,N-dimethyl formamide to provide crystal of 6,7-dihydro-9-fluoro-1-oxo-5-trifluoromethyl-1H,5H-benzo[ij]quinolizine-2-carboxylic acid, m.p. 295°–297° C.

Analysis: Calculated for $C_{14}H_9F_4NO_3$: C, 53.3; H, 2.9; N, 4.4. Found: C, 53.1; H, 2.8; N, 4.4.

EXAMPLE 61

Starting with 2,4-dimethyltetrahydroquinoline, the method of Example 60 is used to prepare white crystals of 6,7-dihydro-5,7-dimethyl-1-oxo-1H,5H-benzo[ij]-quinolizine-2-carboxylic acid (m.p. 269°–272° C.) after recrystallization from a N,N-dimethyl formamide-water mixture.

Analysis: Calculated for $C_{15}H_{15}NO_3$: C, 70.0; H, 5.9; N, 5.5. Found: C, 70.0; H, 5.8; N, 5.4.

Additional compounds are prepared using the method of Example 60 and starting with the appropriately substituted tetrahydroquinolines and are shown in Table VI.

TABLE VI

| Ex. No. | Compound | Melting Point (in ° C.) |
|---|---|---|
| 62 | 9-chloro-6,7-dihydro-1-oxo-5-trifluoromethyl-1H,5H-benzo[ij]quinolizine-6-carboxylic acid | 275–277 |
| 63 | 6,7-dihydro-9-methoxy-1-oxo-5-trifluoromethyl-1H,5H-benzo[ij]quinolizine-2-carboxylic acid | 249–251 |
| | and the intermediate ethyl 6,7-dihydro-9-methoxy-1-oxo-5-trifluoromethyl-1H,5H-benzo[ij]quinolizine-2-carboxylate | 212–214 |
| 64 | 6,7-dihydro-1-oxo-5-trifluoromethyl-1H,5H-benzo[ij]quinolizine-2-carboxylic acid | |
| 65 | 6,7-dihydro-5,6-dimethyl-9-fluoro-1-oxo-1H,5H-benzo[ij]quinolizine-2-carboxylic acid | 234–236 |
| 66 | 6,7-dihydro-5,6-dimethyl-1-oxo-1H,5H-benzo[ij]quinolizine-2-carboxylic acid | 203–206 |

EXAMPLE 67

5-Amino-2,6-dimethyltetrahydroquinoline (2.5 g., 0.014 mole) is mixed with diethyl ethoxymethylenemalonate (6.2 g., 0.028 mole), and the mixture is heated with occasional stirring at 110°–120° C. for 1.5 hours. Polyphosphoric acid (10 g.) is added, and the solution is heated for five minutes at 110°–120° C. The hot solution is poured into 300 ml. of water. The solid precipitate which forms is isolated by filtration and mixed with 200 ml. of 3 percent sodium hydroxide solution. Ethanol (100 ml.) is added while heating the mixture for one-half hour at 100° C. The solution is treated with decolorizing charcoal, filtered and acidified to pH 3 to 4 with concentrated hydrochloric acid. The yellow precipitate is separated by filtration, washed with water and recrystallized from a N,N-dimethyl formamide-water mixture twice to provide 10-amino-6,7-dihydro-5,9-dimethyl-1-oxo-1H,5H-benzo[ij]quinolizine-2-carboxylic acid, m.p. 264°–266° C.

Analysis: Calculated for $C_{15}H_{16}N_2O_3$: C, 66.2; H, 5.9; N, 10.3. Found: C, 65.2; H, 5.9; N, 10.0.

EXAMPLE 68

Using the method of Example 1, 7-acetamido-6-chloro-1,2,3,4-tetrahydroquinoline is converted to 8-amino-9-chloro-6,7-dihydro-5-methyl-1-oxo-1H,5H-benzo[ij]quinolizine-2-carboxylic acid, m.p. >300° C.

The following novel tetrahydroquinoline intermediates are oils at room temperature which were prepared from known compounds by reductive dehalogenation as described broadly hereinabove, identified by infrared spectral analysis and used as oils without further purification:

4-Chloro-6-fluoroquinaldine was reduced with rhodium on carbon to give 6-fluoro-2-methyltetrahydroquinoline.

4,6-Dichloroquinaldine was reduced with rhodium on carbon to give 6-chloro-2-methyltetrahydroquinoline.

6-Methoxyquinaldine was reduced with rhodium on carbon to give 6-methoxy-2-methyltetrahydroquinoline.

6-(N,N-Dimethylamino)quinaldine was reduced with rhodium on carbon to give 6-(N,N-dimethylamino)-2-methyltetrahydroquinoline.

5-Chloro-6-methylquinaldine was reduced with platinum on carbon to give 5-chloro-2,6-dimethyltetrahydroquinoline.

4-Chloro-5-methoxyquinaldine was reduced with platinum on carbon to give 5-methoxy-2-methyltetrahydroquinoline.

4-Chloro-6-fluoro-2-trifluoromethylquinoline was reduced with platinum on carbon to give 6-fluoro-2-trifluoromethyltetrahydroquinoline.

4-Chloro-6-methoxy-2-trifluoromethylquinoline was reduced with platinum on carbon to give 6-methoxy-2-trifluoromethyltetrahydroquinoline.

4,6-Dichloro-2-trifluoromethylquinoline was reduced with platinum on carbon to give 6-chloro-2-trifluoromethyltetrahydroquinoline.

EXAMPLE 69

5-Chloro-2-methyltetrahydroquinoline is condensed with an equimolar amount of diethyl ethoxymethylenemalonate according to the method of Example 1. The ester intermediate of Formula III is isolated and has m.p. 171°–173° C. It is hydrolyzed according to Example 1, and the crystalline solid product is 8-chloro-6,7-dihydro-5-methyl-1-oxo-1H,5H-benzo[ij]quinolizine-2-carboxylic acid, m.p. 277°–279° C.

EXAMPLE 70

A mixture of 75 ml. of 6N hydrochloric acid and 10-amino-6,7-dihydro-5-methyl-1-oxo-benzo[ij]quinolizine-2-carboxylic acid (12.9 g., 0.05 mole) is diazotized at 5° to 10° C. with sodium nitrite (4.14 g., 0.06 mole) dissolved in about 10 ml. of water. The cold mixture is filtered, then it is added to a mixture of cuprous chloride (19.7 g., 0.1 mole) and concentrated hydrochloric acid (150 ml.) while maintaining the temperature below 20° C. After stirring one hour the mixture is diluted with water to provide a creamy-white solid which is collected by filtration. Two recrystallizations from N,N-dimethyl formamide provide 10-chloro6,7-dihydro-5-methyl-1-oxo-1H,5H-benzo[ij]quinolizine-2-carboxylic acid, m.p. 219.5°–222° C.

EXAMPLE 71

A mixture of 70 ml. of 6N hydrochloric acid and 10amino-6,7-dihydro-5-methyl-1-oxo-benzo[ij]quinolizine-2-carboxylic acid (10 g., 0.039 mole) is treated at 0° to 5° C. with sodium nitrite (2.7 g., 0.39 mole) in 10 ml. of water. The solution is stirred for about ten minutes, then neutralized by the addition of solid sodium carbonate. A solution of cuprous chloride (4.7 g., 0.048 mole) in 20 ml. of water and sodium cyanide (4.75 g., 0.097 mole) in 10 ml. of water is cooled to 0° C., then the diazonium solution is added dropwise with vigorous stirring. After stirring for 30 minutes at 0° C. the mixture is heated at 50° C. for 15 minutes, then stirred at about 25° C. for about 65 hours. The solution is acidified to pH 6 with glacial acetic acid to provide a brown solid which is collected by filtration, washed with water, then extracted into two 200 ml. portions of boiling dichloroethane. The hot dichloroethane extracts are filtered, then the filtrate is concentrated to provide an orange solid. The solid is washed thoroughly with hexane, recrystallized from N,N-dimethyl formamide, dissolved in dilute base, reprecipitated with glacial acetic acid and recrystallized again from N,N-dimethyl formamide to provide 10-cyano-6,7-dihydro-5-methyl-1-oxo-1H,5H-benzo[ij]quinolizine-2-carboxylic acid, m.p. >300° C.

EXAMPLE 72

6-Acetamido-4-chloro-2-methylquinoline is reduced catalytically to the novel compound 6-acetamido-2-methyl-1,2,3,4-tetrahydroquinoline. The tetrahydroquinoline is condensed with diethyl ethoxymethylenemalonate by heating without a solvent for one hour at 140° C. Polyphosphoric acid is added, and the solution is heated at 100° C. for one-half hour. The product, 9-amino-6,7-dihydro-5-methyl-1-oxo-1H,5H-benzo[ij]quinolizine-2-carboxylic acid is reacted with acetic anhydride as described in Example 49 to provide 9-acetamido-6,7-dihydro-5-methyl-1-oxo-1H,5H-benzo[ij]quinolizine-2-carboxylic acid, m.p. >310° C. The product is characterized by spectral analysis and elemental analysis, which are found to be consistent with the indicated structure.

What is claimed is:
1. A compound having the formula

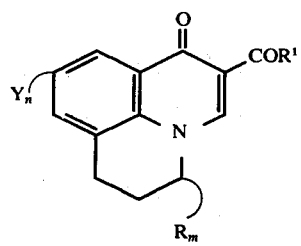

wherein Y is lower alkyl, lower alkoxy, halogen, hydroxy, nitro, cyano, trifluoromethyl, amino, lower alkanamido, trifluoroacetamido or N,N-lower dialkylamino; R is methyl, ethyl or trifluoromethyl; n is zero, one or two; m is zero, one or two, and when R is trifluoromethyl, m is one; and $R^1$ is halogen, amino, lower alkylamido, N,N-lower dialkylamino hydrazino, morpholino or piperidino.

2. The compound 6,7-dihydro-9-fluoro-5-methyl-1-oxo-1H,5H-benzo[ij]quinolizine-2-carboxyl chloride according to claim 1.

3. The compound N,N-dimethyl-6,7-dihydro-9-fluoro-5-methyl-1-oxo-1H,5H-benzo[ij]quinolizine-2-carboxamide according to claim 1.

4. The compound 6,7-dihydro-9-fluoro-5-methyl-1-oxo-1H,5H-benzo[ij]quinolizine-2-carboxylic acid morpholine amide according to claim 1.

5. The compound 6,7-dihydro-9-fluoro-5-methyl-1-oxo-1H,5H-benzo[ij]quinolizine-2-carboxylic acid hydrazide according to claim 1.

* * * * *

UNITED STATES PATENT AND TRADEMARK OFFICE
CERTIFICATE OF CORRECTION

PATENT NO. : 4,014,877
DATED : March 29, 1977
INVENTOR(S) : JOHN F. GERSTER

It is certified that error appears in the above-identified patent and that said Letters Patent are hereby corrected as shown below:

Col. 3, line 24, change "into" to -- onto --.

Col. 3, line 35 (#5), insert asterisk after "sp."

Col. 12, line 36, change "227°" to -- 277° --.

Signed and Sealed this

First Day of November 1977

[SEAL]

Attest:

RUTH C. MASON
Attesting Officer

LUTRELLE F. PARKER
Acting Commissioner of Patents and Trademarks